United States Patent
Radhakrishnan et al.

(10) Patent No.: US 10,413,300 B2
(45) Date of Patent: Sep. 17, 2019

(54) COLLATERAL FLOW CHANNEL SEALANT DELIVERY METHODS AND SYSTEMS

(71) Applicant: PulmonX Corporation, Redwood City, CA (US)

(72) Inventors: Sri Radhakrishnan, Cupertino, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 511 days.

(21) Appl. No.: 15/182,453

(22) Filed: Jun. 14, 2016

(65) Prior Publication Data
US 2016/0367259 A1 Dec. 22, 2016

Related U.S. Application Data (60) Provisional application No. 62/183,170, filed on Jun. 22, 2015.

(51) Int. Cl.
*A61B 5/08* (2006.01)
*A61B 17/12* (2006.01)
(Continued)

(52) U.S. Cl.
CPC .......... *A61B 17/12104* (2013.01); *A61B 5/08* (2013.01); *A61B 5/4848* (2013.01);
(Continued)

(58) Field of Classification Search
CPC .. A61B 17/12; A61B 1/04; A61B 1/06; A61B 1/313; A61B 17/122; A61B 17/128;
(Continued)

(56) References Cited

U.S. PATENT DOCUMENTS 4,351,344 A   9/1982 Stenzler
7,798,147 B2  9/2010 Hendrinksen et al.
(Continued)

FOREIGN PATENT DOCUMENTS

WO   WO 2009/135070 A1   11/2009

OTHER PUBLICATIONS

Dernevik, et al. Initial experience with the world's first digital drainage system. The benefits of recording air leaks with graphic representation. Eur J Cardiothorac Surg. Feb. 2007;31(2):209-13. Epub Dec. 27, 2006.
(Continued)

*Primary Examiner* — Navin Natnithithadha
*Assistant Examiner* — Eric J Messersmith
(74) *Attorney, Agent, or Firm* — Wilson Sonsini Goodrich & Rosati (57) ABSTRACT

Devices, methods, and systems are provided for occluding a collateral flow channel between a target lung compartment and an adjacent lung compartment. A video-assisted thoracoscopic device is inserted into a thoracic cavity of a patient and positioned at a fissure between a target lung compartment and an adjacent lung compartment. A collateral flow channel between the target lung compartment and the adjacent lung compartment is then identified using the video-assisted thoracoscopic device and an agent is injected into the collateral flow channel, thereby reducing the collateral flow channel.

13 Claims, 6 Drawing Sheets

(51) Int. Cl.
*A61B 5/00* (2006.01)
*A61M 25/10* (2013.01)
*A61M 25/01* (2006.01)
*A61M 16/04* (2006.01)
*A61M 25/00* (2006.01)
*A61F 2/04* (2013.01)

(52) U.S. Cl.
CPC .... *A61B 17/1204* (2013.01); *A61B 17/12136* (2013.01); *A61M 16/042* (2014.02); *A61M 16/0406* (2014.02); *A61M 16/0459* (2014.02); *A61M 25/0147* (2013.01); *A61M 25/10* (2013.01); *A61F 2002/043* (2013.01); *A61F 2250/0067* (2013.01); *A61M 2025/0001* (2013.01); *A61M 2202/0413* (2013.01); *A61M 2202/0468* (2013.01); *A61M 2205/502* (2013.01)

(58) Field of Classification Search
CPC ....... A61B 5/00; A61B 5/08; A61B 17/12104; A61B 5/4848; A61B 17/1204; A61B 17/12136; A61F 2/04; A61F 2002/043; A61F 2250/0067; A61M 16/20; A61M 25/01; A61M 25/10; A61M 5/158; A61M 25/0147; A61M 16/0406; A61M 16/042; A61M 16/0459; A61M 2202/0468; A61M 2202/0413; A61M 2025/0001; A61M 2205/502

See application file for complete search history.

(56) References Cited

U.S. PATENT DOCUMENTS

| | | |
|---|---|---|
| 7,883,471 B2 | 2/2011 | Aljuri et al. |
| 8,136,526 B2 | 3/2012 | Perkins et al. |
| 9,364,168 B2 | 6/2016 | Mantri |
| 2003/0051733 A1 | 3/2003 | Kotmel et al. |
| 2004/0200484 A1* | 10/2004 | Springmeyer ... A61B 17/12022 128/898 |
| 2007/0043350 A1* | 2/2007 | Soltesz ............... A61B 18/082 606/41 |
| 2007/0142742 A1 | 6/2007 | Aljuri et al. |
| 2008/0027343 A1 | 1/2008 | Fields et al. |
| 2011/0201956 A1 | 8/2011 | Alferness et al. |
| 2012/0150057 A1 | 6/2012 | Mantri |

OTHER PUBLICATIONS

Office action dated Oct. 8, 2013 for U.S. Appl. No. 13/174,665.
Office action dated Apr. 21, 2014 for U.S. Appl. No. 13/174,665.
Office action dated Jan. 27, 2015 for U.S. Appl. No. 13/174,665.
Notice of allowance dated Feb. 17, 2015 for U.S. Appl. No. 13/174,665.

* cited by examiner

COLLATERAL FLOW CHANNEL SEALANT DELIVERY METHODS AND SYSTEMS

CROSS-REFERENCE TO RELATED APPLICATIONS

This application claims the benefit of U.S. Provisional No. 62/183,170, filed Jun. 22, 2015, the entire content of which is incorporated herein by reference in its entirety.

FIELD OF THE INVENTION

Present disclosure relates generally to devices, methods, and systems for delivering an agent to a lung region.

BACKGROUND

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, a delivery catheter is used to implant one or more implantable devices in airways feeding a diseased region of the lung to regulate fluid flow to the diseased lung region in order to fluidly isolate the region of the lung. These implantable devices can be, for example, one-way valves that allow flow in the exhalation direction only, occluders or plugs that prevent flow in either direction, or two-way valves that control flow in both directions.

In addition to the above, it is sometimes desirable to provide methods for sealing collateral flow channels between adjacent lung segments. Such sealing methods may be particularly useful for treating patients prior to endobronchial or other lung volume reduction procedures. Thus, methods and apparatus for sealing collateral flow channels should be compatible with known protocols for occluding diseased lung segments and regions for performing lung volume reduction, including the placement of plugs and occluding members within the airways leading to such diseased lung segments and regions. One such sealing method and system has been described in U.S. Pat. No. 8,137,302. In other cases, sealing agents may be provided, though they are not equipped with the systems or methods for delivery for collateral channels. Other such sealing agents have been used in U.S. Pat. Nos. 7,819,908 and 8,445,589. The objective thus remains to provide additional methods for sealing collateral channels. At least some of these objectives will be met by the inventions described herein below.

SUMMARY OF THE INVENTION

The present disclosure relates to aspects of methods, and systems for occluding a collateral flow channel. In one aspect, a method for occluding a collateral flow channel between a target lung compartment and an adjacent lung compartment is disclosed. Said method comprises inserting a video-assisted thoracoscopic device into a thoracic cavity of a patient, positioning the video-assisted thoracoscopic device at a fissure between a target lung compartment and an adjacent lung compartment, identifying a collateral flow channel between the target lung compartment and the adjacent lung compartment using the video-assisted thoracoscopic device, inserting a needle into tissue forming the collateral flow channel, and injecting an agent through the needle and into the collateral flow channel, thereby reducing the collateral flow channel. The agent is may be a sealant.

The above method may further comprise placing a clip on the collateral channel thereby pinching closed the collateral channel. The clip may be a normally closed clip. Alternatively, the method may comprise cutting tissue at the collateral flow channel thereby disrupting the collateral flow channel.

Additionally, the target lung compartment may be accessed using an endobronchial isolation catheter. The target lung compartment may then be isolated using the endobronchial isolation catheter. Pressure and/or flow may be measured within the target lung compartment. Sealing of the collateral flow channel may then be verified based on the measured pressure or flow.

The method may further comprise placing an endobronchial valve within an airway leading to the target lung compartment. The endobronchial valve may be a one-way flow control valve configured to allow air to flow out of the target lung compartment and prevent air flow into the target lung compartment.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION OF THE INVENTION

Although the detailed description contains many specifics, these should not be construed as limiting the scope of the disclosure but merely as illustrating different examples and aspects of the disclosure. It should be appreciated that the scope of the disclosure includes other embodiments not discussed herein. Various other modifications, changes and variations which will be apparent to those skilled in the art may be made in the arrangement, operation and details of the method, device, and system of the present embodiments disclosed herein without departing from the spirit and scope of the disclosure as described here.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Throughout this disclosure, reference is made to the term "agent". As used herein, the term "agent" refers to a sealing agent. For purposes of this application, the term "agent" is interchangeable with "sealant" and "sealing agent."

Throughout this disclosure, reference is made to the term "lung region". As used herein, the term "lung region" refers to a defined division or portion of a lung. For exemplary purposes, lung regions are described herein with reference to human lungs, wherein some exemplary lung regions include lung lobes and lung segments. Thus, the term "lung region" as used herein can refer, for example, to a lung lobe or a lung segment. Such nomenclature conforms to nomenclature for portions of the lungs that are known to those skilled in the art. However, it should be appreciated that the term "lung region" does not necessarily refer to a lung lobe or a lung segment, but can refer to some other defined division or portion of a human or non-human lung.

The present disclosure describes a method for sealing a collateral flow channel between a target lung compartment and an adjacent lung compartment. The method comprises navigating a video-assisted thoracoscopic surgical (VATS) device to a fissure between the target lung compartment and the adjacent lung compartment and identifying a collateral flow channel. Thereafter, an agent, such as a sealant, is injected into the collateral flow channel, thereby sealing the collateral flow channel. Additionally, systems comprising the application of these methods are also described.

Figure 1A:
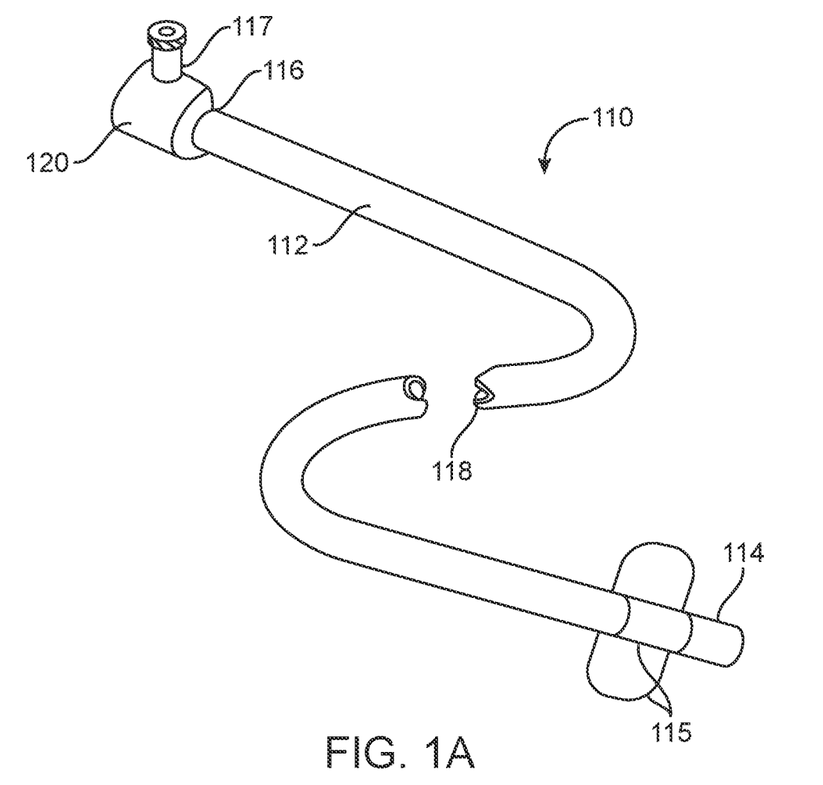
FIG. 1A is a perspective view of one embodiment of an agent delivery catheter.
Figure 1B:
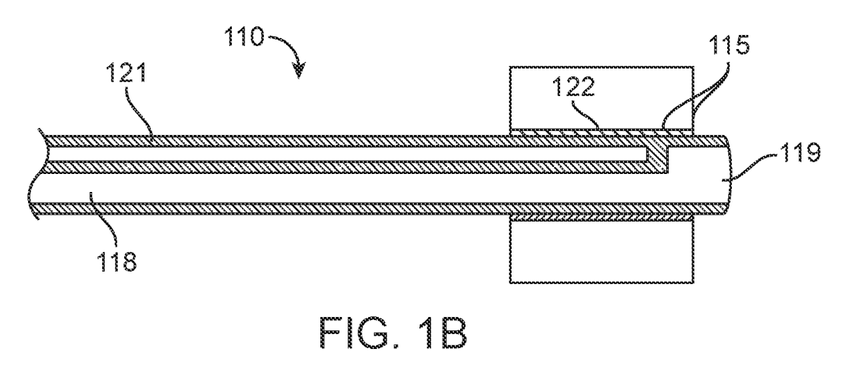
FIG. 1B is an axial, cross-sectional view of a distal portion of one embodiment of an agent delivery catheter comprising a central lumen for delivery of fluid.

Turning to the figures, FIG. 1A shows a catheter for use in conjunction with the present disclosure. Similar delivery catheters have been described in U.S. Pat. Nos. 8,137,302 and 7,883,471, which are incorporated herein by reference. Delivery catheter 110 comprises an elongate catheter body 112 having a proximal end 116, and a distal end 114 that comprises an occlusion element 115, which in this case is an inflatable balloon. Catheter body 112 includes at least one central lumen or passage 118 with a distal opening 119 (shown in greater detail in FIG. 1B). A hub 120 is disposed at the proximal end 116 of the catheter body 112 and includes at least one port 117 for connection to an inflation lumen 121 which feeds an inflation medium to the expandable element 115, for sealing the distal end of the catheter within a lung airway. In the embodiment shown in FIG. 1B, catheter 110 comprises a central lumen or passage 118 for delivery of fluid. The balloon inflation lumen 121 opens through a port 122 to deliver the inflation medium to the expandable member 115. Although not illustrated, catheter 110 may be provided with other features, such as sensors disposed within or in-line with the catheter. Additionally, the catheter may be provided with pull wires or other mechanisms for steering the distal ends of the catheters in order to facilitate advancement through the branching airways of the lung. Still further additionally, the catheters 110 may be provided with optical fibers, small CCD's or other cameras, or other means at their distal ends for visualizing advancement of the catheters through the airways. The catheter body may be composed of conventional catheter materials to provide the desired flexibility and biocompatibility. Suitable materials include PTFE, PVC, polyurethane, PET, polypropelene or other polymer alloys or interpenetrating network polymers (IPNs) with or without metallic and/or ceramic braid or support. Using such materials, the catheters may be formed by conventional extrusion techniques.

Figure 2:
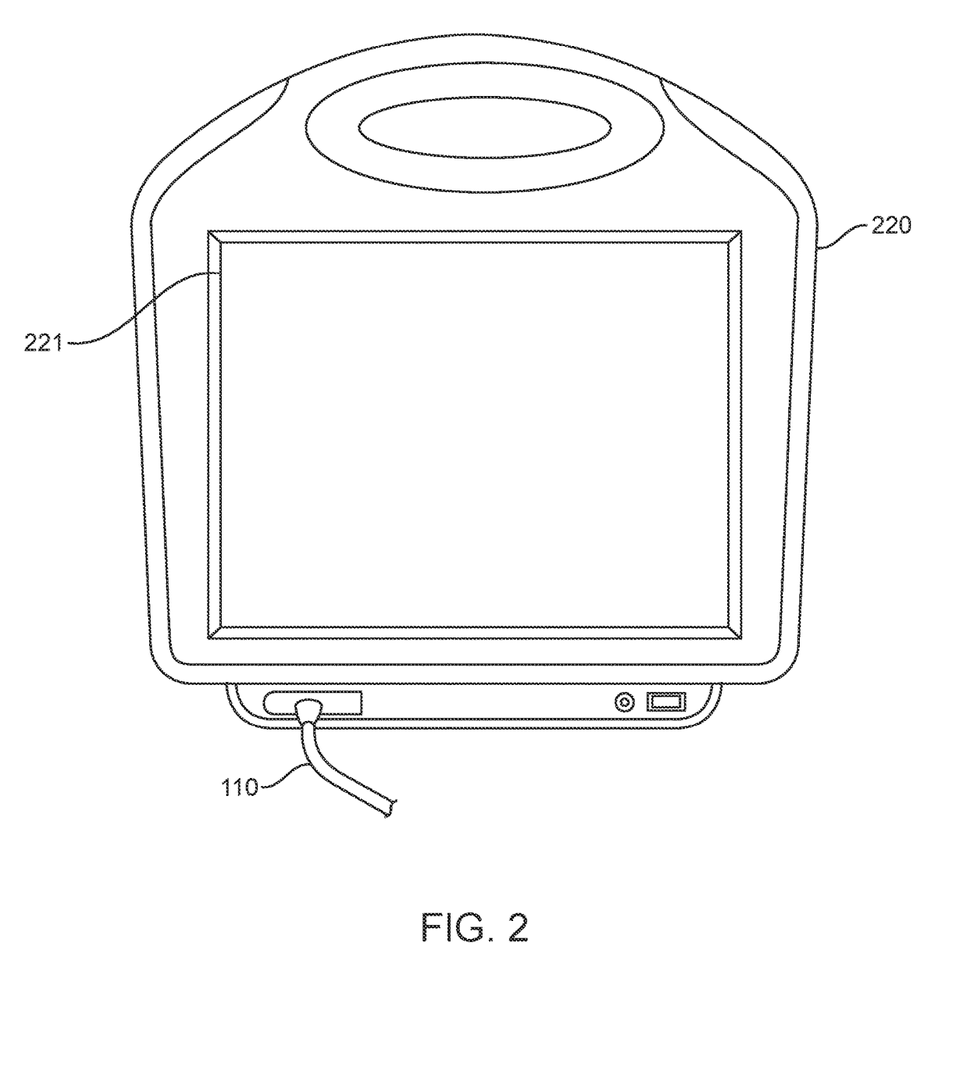
FIG. 2 shows one embodiment of a lung segment assessment system.

Further, as shown in FIG. 2, the catheter 110 terminates at or is in-line with unit 220 that may include components such as a display unit, a user feedback mechanism and a processor. In this embodiment, the display unit comprises a screen 221 showing input from the one or more sensors within or in-line with the catheter. The user feedback mechanism comprises a mechanism for user input, such as a touchscreen 221. Other user feedback mechanisms may include knobs, dials, buttons, or any other such mechanism. The processor (not shown) is internal or otherwise associated with unit 220 and is configured to perform functions such as receive, process, calculate or relay input from the sensor. Additionally, the unit 220 may comprise or may be associated with a fluid delivery mechanism (not shown) configured to deliver a fluid (e.g., a gas) via the catheter into the target lung compartment. Further, the processor of the unit is equipped to execute various functions. Such functions may include releasing fluid, releasing an agent, timing the release of the fluid or the agent to a predetermined event or user input, measuring input from a sensor, calculating input from a sensor and relaying input or calculations to a display.

The respiratory system of the patient starts at the mouth and extends through the vocal cords and into the trachea where it then joins the main stem bronchi which leads into the lungs, which are comprised of various segments. Each lung segment, also referred to as a bronchopulmonary segment, is an anatomically distinct unit or compartment of the lung which is fed air by a tertiary bronchus and which oxygenates blood through a tertiary artery. Normally, the lung segment and its surrounding fibrous septum (lung walls) are intact units which can be surgically removed or separated from the remainder of the lung without interrupting the function of the surrounding lung segments.

The presence of collateral flow channels in the fibrous septum or wall of a diseased lung segment is problematic since the diseased segment cannot be removed or even isolated successfully with the collateral channels intact. In the case of isolation and deflation of the diseased lung segment, the presence of the collateral channels will permit the reentry of air as the patient breathes. Thus, the methods described below, by occluding the collateral passages, return a lung wall having collateral ventilation into a functionally intact lung wall which permits subsequent treatment of diseased regions using endobronchial or other treatment protocols.

Figure 3:
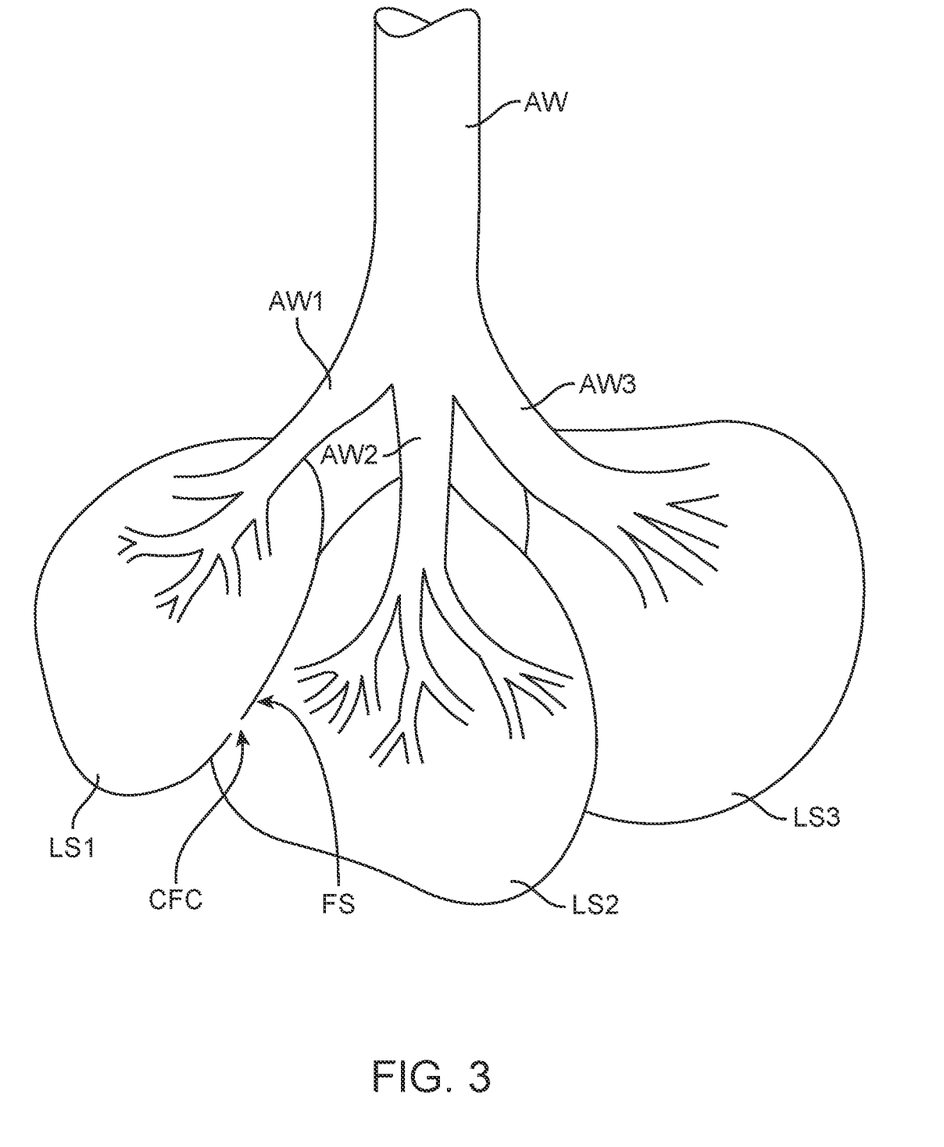
FIG. 3 shows a lung segment having a collateral flow channel.

As seen in FIG. 3, the individual lobes of a lung each comprise a plurality of lung segments LS which are fed by individual branches of the bronchi or airways AW. For example, a first lung segment LS1, a second lung segment LS2, and a third lung segment LS3 may be fed from a single airway AW which divides into three branches AW1, AW2, and AW3, as illustrated in FIG. 3. In the cases of diseased or other compromised lung segments, however, the fibrous septum may comprise collateral flow channels CFC therebetween. The collateral flow channels CFC in the fissure FS between the target lung segment LS1 and the adjacent lung segment LS2 will permit gas flow in either direction prior to the treatments described herein.

Figure 4:
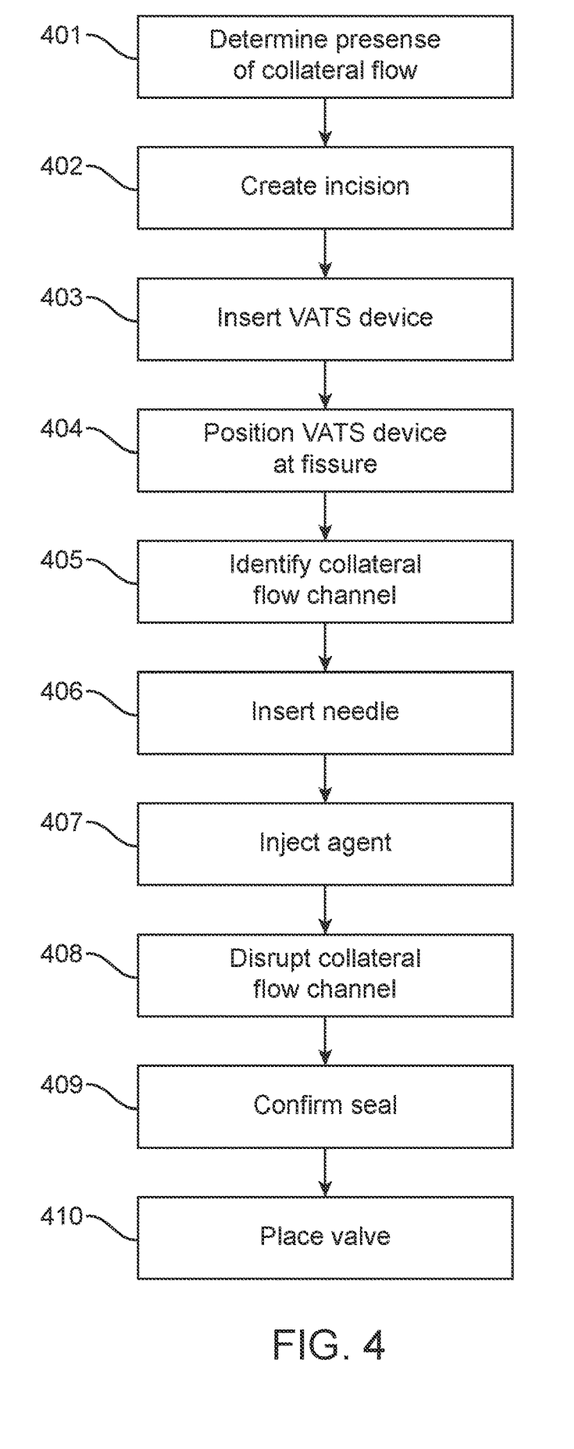
FIG. 4 illustrates one embodiment of a method of delivering an agent.
Figure 5:
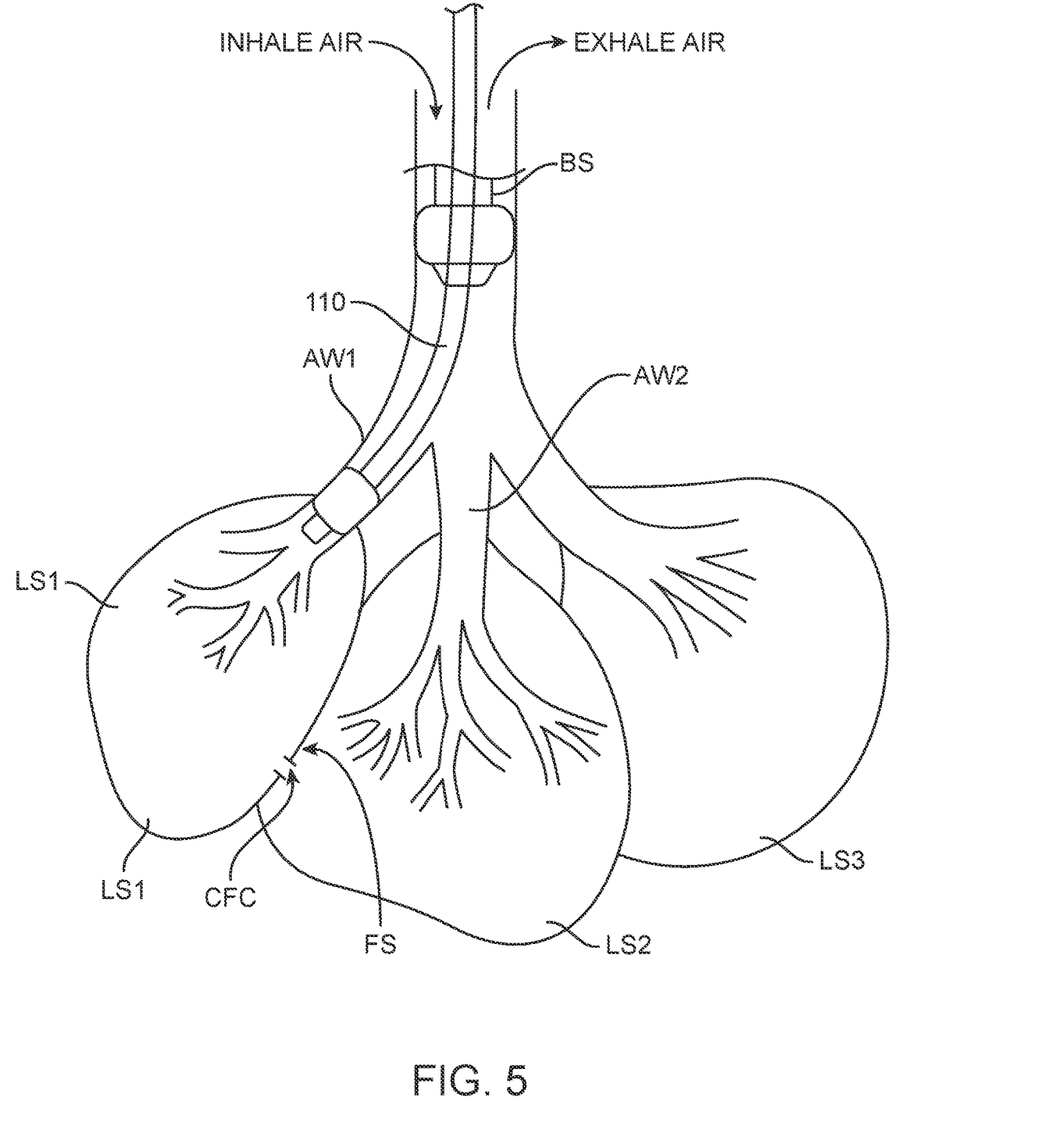
FIG. 5 shows isolation of a target lung segment.

FIGS. 5-7B show the practice of the methods described in FIG. 4. Optionally, at step 401 the target lung segment LS1 may be assessed to determine if collateral flow is present. Referring now to FIG. 5, the catheter 110 is positioned in the airway AW1 leading into the target lung segment LS1. By expanding the expandable member 115 in the first airway AW1, the first lung segment LS1 is isolated, and this isolation is compromised only by any collateral flow channels CFC that allow air to leak in from adjacent lung segments AW2. Thereafter, pressure and/or flow within the target lung segment LS1 is measured. The presence of collateral flow is then determined based on the measured pressure and/or flow. Determination of collateral flow is disclosed in U.S. Pat. No. 7,883,471 and U.S. Pub. Nos. 2008/0027343, 2003/0051733, 2007/0142742, 2012/0149995, all of which are hereby incorporated by reference.

At step 402, one or more incisions are made in the chest of a patient. The incisions may be made at various locations between the ribs. In one embodiment a separate incision is made for a VATS device 601, an injection device 602, and a cutting or closing device. In another embodiment one or more devices may share a single incision.

A VATS device 601 is inserted, at step 403, through the incision and into the thoracic cavity of the patient. The VATS device 601 may be a thoracoscope comprising a light source and a video camera configured to transmit video to an external monitor.

At step 404, the distal tip of the VATS device 601 is positioned at a fissure FS between a target lung compartment and an adjacent lung compartment. Thereafter, at step 405, a collateral flow channel CFC between the target lung compartment and the adjacent lung compartment is identified using the VATS device 601. In one embodiment, the presence of collateral flow is determined in the target lung segment before the collateral flow channel CFC is identified using the VATS device 601. In another embodiment, the collateral flow channel CFC is identified using the VATS device 601 without first determining that collateral flow is present.

Figure 6:
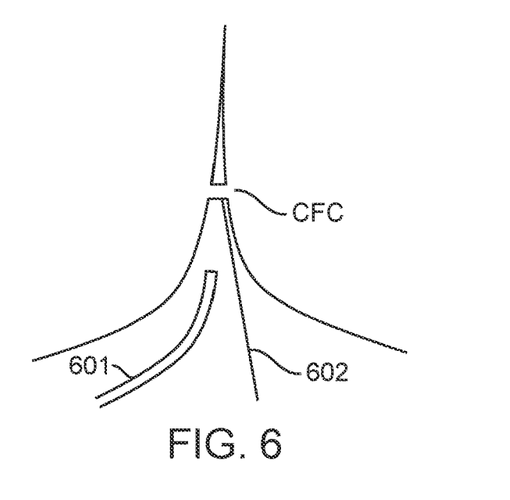
FIG. 6 shows the delivery of an agent to a collateral flow channel.

At step 406, a needle 602 is inserted into tissue forming the collateral flow channel CFC. An agent is then injected through the needle 602 into the collateral flow channel CFC at step 407 thereby reducing or sealing the collateral flow channel CFC. The agent may take any form such as a gel, particles, aerosol, liquid, or autologous blood.

Figure 7A:
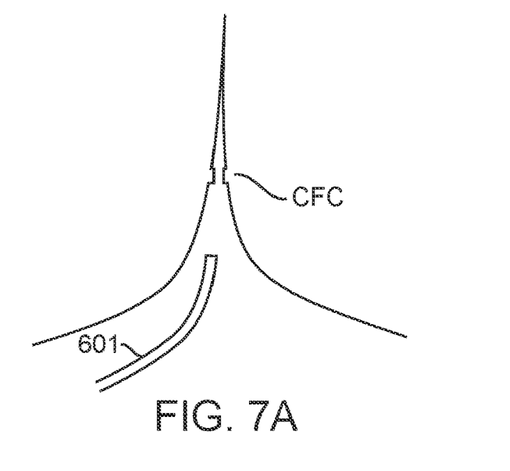
FIGS. 7A and 7B show exemplary disruption of collateral flow channels.
Figure 7B:
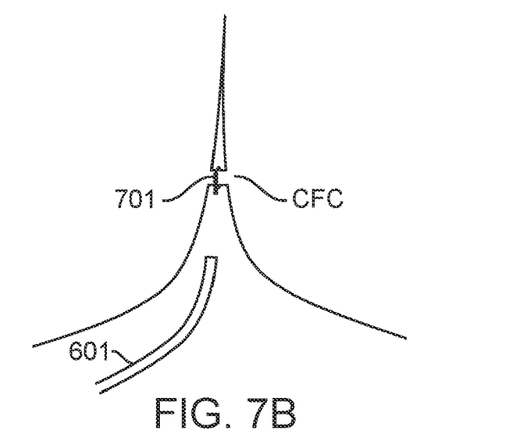

Additionally, at step 408, the collateral flow channel CFC may be disrupted. In one embodiment, as seen in FIG. 7A, tissue forming the collateral flow channel CFC is cut, thereby severing the collateral flow channel CFC. The agent previously injected into the collateral flow channel CFC will seal the cut therefore preventing the air from entering or exiting through the incision. The cut may also be sealed using staples, sutures, or other surgical methods. In another embodiment, as seen in FIG. 7B, a clip 701 may be placed on the collateral flow channel CFC thereby pinching closed the collateral flow channel CFC. The clip 701 may comprise one or more atraumatic portions configured to reduce tissue trauma once the contact elements have engaged with tissue. In an embodiment, the clip 701 is a normally closed clip. In other embodiments, the collateral flow channel CFC may be disrupted using sutures or staples.

Optionally, at step 409, the target lung compartment may be assessed to confirm that the collateral flow channel CFC has been sealed and/or to confirm that no other collateral flow is present. As with step 401, the catheter 110 is positioned in the airway AW1 leading into the target lung segment LS1. The expandable member 115 is expanded in airway AW1 thereby isolating the target lung segment LS1. Thereafter, pressure and/or flow within the target lung compartment is measured and the presence or absence of collateral flow is determined based on the measured pressure and/or flow to confirm that the collateral flow channel CFC has been sealed and that no other collateral flow is present.

At step 410, an endobronchial valve may be placed within the airway AW1 leading to the target lung segment LS1. In an embodiment, the endobronchial valve is a one-way flow control valve configured to allow air to flow out of the target lung compartment and prevent air flow into the target lung compartment, thus causing volume reduction or collapse of the target lung region. Examples of such methods and implants are described, for example, in U.S. patent application Ser. No. 11/682,986 and U.S. Pat. No. 7,798,147, the full disclosures of which are hereby incorporated by reference. In addition, a plug may be placed in the airway.

While the above is a complete description of various embodiments, any of a number of alternatives, modifications, and equivalents may be used in alternative embodiments. Therefore, the above description should not be taken as limiting the scope of the invention as it is defined by the appended claims.

What is claimed is:

1. A method for occluding a collateral flow channel between a target lung compartment and an adjacent lung compartment, said method comprising:

inserting a video-assisted thoracoscopic device into a thoracic cavity of a patient;
positioning the video-assisted thoracoscopic device at a fissure between a target lung compartment and an adjacent lung compartment;
identifying a collateral flow channel between the target lung compartment and the adjacent lung compartment using the video-assisted thoracoscopic device;
inserting a needle into the thoracic cavity and through tissue forming the collateral flow channel; and
injecting an agent through the needle and into the collateral flow channel, thereby reducing the collateral flow channel.

2. The method of claim 1, further comprising placing a clip on the collateral channel thereby pinching closed the collateral channel.

3. The method of claim 2, wherein the clip is a normally closed clip.

4. The method of claim 1, further comprising cutting tissue at the collateral flow channel thereby disrupting the collateral flow channel.

5. The method of claim 1, wherein the collateral flow channel is sealed.

6. The method of claim 1, wherein the agent is a sealant.

7. The method of claim 1, wherein the agent is a sclerosing agent.

8. The method of claim 1, wherein the agent is autologous blood.

9. A method as in claim 1, further comprising:
accessing the target lung compartment using an endobronchial isolation catheter;
isolating the target lung compartment using the endobronchial isolation catheter;
measuring pressure or flow within the target lung compartment; and
verifying the collateral flow channel has been sealed based on the measured pressure or flow.

10. A method as in claim 1, further comprising placing an endobronchial valve within an airway leading to the target lung compartment.

11. A method as in claim 10, wherein the endobronchial valve is a one-way flow control valve configured to allow air to flow out of the target lung compartment and prevent air flow into the target lung compartment.

12. A method for occluding a collateral flow channel between a target lung compartment and an adjacent lung compartment, said method comprising:
inserting a video-assisted thoracoscopic device into a thoracic cavity of a patient;
positioning the video-assisted thoracoscopic device at a fissure between a target lung compartment and an adjacent lung compartment;
identifying a collateral flow channel between the target lung compartment and the adjacent lung compartment using the video-assisted thoracoscopic device;
placing a clip into the thoracic cavity and on the collateral channel thereby pinching closed the collateral channel.

13. A method for occluding a collateral flow channel between a target lung compartment and an adjacent lung compartment, said method comprising:
inserting a video-assisted thoracoscopic device into a thoracic cavity of a patient;
positioning the video-assisted thoracoscopic device at a fissure between a target lung compartment and an adjacent lung compartment; identifying a collateral flow channel between the target lung compartment and the adjacent lung compartment using the video-assisted thoracoscopic device;
cutting tissue at the collateral flow channel from the thoracic cavity thereby disrupting the collateral flow channel.

* * * * *